(12) United States Patent
Bessonov et al.

(10) Patent No.: US 11,329,186 B2
(45) Date of Patent: May 10, 2022

(54) LIGHT-BASED SENSOR APPARATUS AND ASSOCIATED METHODS

(71) Applicant: Nokia Technologies Oy, Espoo (FI)

(72) Inventors: Alexander Bessonov, Cambridge (GB); Darryl Cotton, St. Ives (GB); Adam Robinson, Cambridge (GB)

(73) Assignee: Nokia Technolgies Oy, Espoo (FI)

(*) Notice: Subject to any disclaimer, the term of this patent is extended or adjusted under 35 U.S.C. 154(b) by 212 days.

(21) Appl. No.: 15/770,277

(22) PCT Filed: Oct. 7, 2016

(86) PCT No.: PCT/FI2016/050701
§ 371 (c)(1),
(2) Date: Apr. 23, 2018

(87) PCT Pub. No.: WO2017/072400
PCT Pub. Date: May 4, 2017

(65) Prior Publication Data
US 2018/0315883 A1    Nov. 1, 2018

(30) Foreign Application Priority Data

Oct. 28, 2015  (EP) .................................... 15191911

(51) Int. Cl.
*H01L 31/173* (2006.01)
*H01L 31/024* (2014.01)
(Continued)

(52) U.S. Cl.
CPC .......... *H01L 31/173* (2013.01); *A61B 5/0205* (2013.01); *A61B 5/02433* (2013.01);
(Continued)

(58) Field of Classification Search
CPC .... H01L 31/173; H01L 31/024; A61B 5/0205
(Continued)

(56) References Cited

U.S. PATENT DOCUMENTS 6,097,748 A   8/2000 Huang et al.
6,608,360 B2  8/2003 Starikov et al.
(Continued)

FOREIGN PATENT DOCUMENTS

CN   102646677 A   8/2012
CN   103022072 A   4/2013
(Continued)

OTHER PUBLICATIONS

Meyer et al., "Metal Oxide Induced Charge Transfer Doping and Band Alignment of Graphene Electrodes for Efficient Organic Light Emitting Diodes", Scientific Reports, Jun. 20, 2014, pp. 1-7.
(Continued)

*Primary Examiner* — David P Porta
*Assistant Examiner* — Carolyn Fin
(74) *Attorney, Agent, or Firm* — Harrington & Smith

(57) ABSTRACT

An apparatus (201) comprises a light emitter (202) and a photodetector (203) formed on a single fluid-permeable substrate (206) such that the photodetector (203) is able to detect light emitted by the light emitter (202) after interaction of the light with a user of the apparatus (201). The photodetector comprises a channel member (207) which may be made from graphene, respective source and drain electrodes (208, 209), a layer of photosensitive material (210) configured to vary the flow of electrical current through the channel member (207) on exposure to light from the light emitter (202), and a gate electrode (211). The apparatus (201) further comprises a layer of fluid-impermeable dielectric material (212) configured to inhibit a flow of electrical current between the channel member (207) and the gate electrode (211) of the photodetector (203) to enable the electrical conductance of the channel member (207) to be controlled by a voltage applied to the gate electrode (211) and to inhibit exposure of the light emitter (202) to fluid which has permeated through the fluid-permeable substrate (206). The layer of fluid-impermeable dielectric material
(Continued)

(212) allows resilient substrates made from polymeric material to be used without the risk of damage to the overlying components caused by the permeated fluid. The dual functionality of the layer of fluid-impermeable dielectric material (212) reduces the number of fabrication steps used to form the apparatus (201) and results in a thinner, more compact device.

20 Claims, 4 Drawing Sheets

(51) Int. Cl.

| | | |
|---|---|---|
| *H01L 31/113* | (2006.01) |
| *A61B 5/024* | (2006.01) |
| *A61B 5/1455* | (2006.01) |
| *A61B 5/0205* | (2006.01) |
| *A61B 5/00* | (2006.01) |
| *H01L 27/32* | (2006.01) |
| *A61B 5/021* | (2006.01) |

(52) U.S. Cl.
CPC .......... *A61B 5/14552* (2013.01); *A61B 5/681* (2013.01); *A61B 5/6898* (2013.01); *H01L 31/024* (2013.01); *H01L 31/1136* (2013.01); *A61B 5/021* (2013.01); *A61B 5/6826* (2013.01); *A61B 2562/0233* (2013.01); *A61B 2562/0238* (2013.01); *A61B 2562/12* (2013.01); *H01L 27/3227* (2013.01)

(58) Field of Classification Search
USPC ...................................................... 250/338.4
See application file for complete search history.

(56) References Cited

U.S. PATENT DOCUMENTS

| | | | |
|---|---|---|---|
| 8,053,782 B2 | 11/2011 | Avouris et al. |
| 8,519,450 B1 * | 8/2013 | Zhu .................. H01L 29/84 |
| | | | 257/254 |
| 9,040,998 B2 | 5/2015 | Tsurume et al. |
| 9,936,574 B2 * | 4/2018 | Rogers ................ A61B 5/6867 |
| 2002/0056852 A1 | 5/2002 | Scott et al. |
| 2003/0218119 A1 | 11/2003 | Stegmuller |
| 2006/0146904 A1 | 7/2006 | Guenter et al. |
| 2010/0283044 A1 | 11/2010 | Inoue |
| 2012/0006978 A1 | 1/2012 | Ludwig |
| 2012/0213466 A1 | 8/2012 | Golubovic et al. |
| 2012/0326143 A1 | 12/2012 | Tsurume et al. |
| 2013/0075761 A1 | 3/2013 | Akiyama |

FOREIGN PATENT DOCUMENTS

| | | |
|---|---|---|
| CN | 103681938 A | 3/2014 |
| EP | 3131121 A1 | 2/2017 |
| EP | 3136443 A1 | 3/2017 |
| EP | 3136445 A1 | 3/2017 |
| EP | 3147954 A1 | 3/2017 |
| WO | 2007/051753 A1 | 5/2007 |
| WO | 2010/090519 A2 | 8/2010 |
| WO | 2014/149004 A1 | 9/2014 |

OTHER PUBLICATIONS

Chang et al., "Solution-Processed Transparent Blue Organic Light-Emitting Diodes with Graphene as the Top Cathode", Scientific Reports, Apr. 20, 2015, pp. 1-6.
Withers et al., "Light-Emitting Diodes by Band-Structure Engineering in Van der Waals Heterostructures", Nature Materials, vol. 14, Mar. 2015, pp. 301-306.
Extended European Search Report received for corresponding European Patent Application No. 15191911.5, dated May 24, 2016, 11 pages.
Klekachev et al., "Graphene Transistors and Photodetectors", The Electrochemical Society Interface, vol. 22, No. 1, 2013, pp. 63-68.
International Search Report and Written Opinion received for corresponding Patent Cooperation Treaty Application No. PCT/FI2016/050701, dated Jan. 27, 2017, 19 pages.

* cited by examiner

LIGHT-BASED SENSOR APPARATUS AND ASSOCIATED METHODS

RELATED APPLICATION

This application was originally filed as PCT Application No. PCT/FI2016/050701 filed Oct. 7, 2016 which claims priority benefit from EP Application No. 15191911.5 filed Oct. 28, 2015.

TECHNICAL FIELD

The present disclosure relates particularly to sensors, associated methods and apparatus. Certain embodiments specifically concern an apparatus comprising a light emitter and a photodetector formed on a single fluid-permeable substrate such that the photodetector is able to detect light emitted by the light emitter after interaction of the light with a user of the apparatus. Certain aspects/embodiments may relate to sensors for medical applications, such as $SpO_2$ sensors, blood pressure sensors and pulse sensors. Such sensors may form part of portable electronic devices, in particular, so-called hand-portable electronic devices which may be hand-held in use (although they may be placed in a cradle in use). Such hand-portable electronic devices include so-called Personal Digital Assistants (PDAs) and tablet PCs.

The portable electronic devices/apparatus according to one or more disclosed example aspects/embodiments may provide one or more audio/text/video communication functions (e.g. tele-communication, video-communication, and/or text transmission, Short Message Service (SMS)/Multimedia Message Service (MMS)/emailing functions, interactive/non-interactive viewing functions (e.g. web-browsing, navigation, TV/program viewing functions), music recording/playing functions (e.g. MP3 or other format and/or (FM/AM) radio broadcast recording/playing), downloading/sending of data functions, image capture function (e.g. using a (e.g. in-built) digital camera), and gaming functions.

BACKGROUND

Research is currently being done to develop new sensor devices.

The listing or discussion of a prior-published document or any background in this specification should not necessarily be taken as an acknowledgement that the document or background is part of the state of the art or is common general knowledge.

SUMMARY

According to a first aspect, there is provided an apparatus comprising a light emitter and a photodetector formed on a single fluid-permeable substrate such that the photodetector is able to detect light emitted by the light emitter after interaction of the light with a user of the apparatus, the photodetector comprising a channel member and respective source and drain electrodes configured to enable a flow of electrical current through the channel member between the source and drain electrodes, a layer of photosensitive material configured to vary the flow of electrical current through the channel member on exposure to light from the light emitter, and a gate electrode, wherein the apparatus comprises a layer of fluid-impermeable dielectric material configured to:

inhibit a flow of electrical current between the channel member and the gate electrode of the photodetector to enable the electrical conductance of the channel member to be controlled by a voltage applied to the gate electrode; and inhibit exposure of the light emitter to fluid which has permeated through the fluid-permeable substrate.

The fluid-permeable substrate may comprise one or more resilient polymeric materials. The term "resilient" in this sense may be taken to mean that the one or more polymeric materials are capable of returning at least once to their original form after being bent, compressed, or stretched.

The gate electrode may be embedded within the fluid-permeable substrate, and the layer of fluid-impermeable dielectric material may be positioned between the embedded gate electrode and the channel member.

The layer of fluid-impermeable dielectric material may be configured to facilitate the dissipation of heat produced by the light emitter.

The light emitter and photodetector may be at least partly formed on top of the layer of fluid-impermeable dielectric material, and the fluid-impermeable dielectric material on which the light emitter is at least partly formed may have a different thickness than the fluid-impermeable dielectric material on which the photodetector is at least partly formed.

The layer of fluid-impermeable dielectric material may have a thickness of between 10 and 200 nm, and a surface roughness of less than 1 nm, 5 nm, 10 nm or 25 nm.

The light emitter and photodetector may be formed on the fluid-permeable substrate such that the photodetector is able to detect light emitted by the light emitter after one or more of reflection of the light from a body part of the user and transmission of the light through a body part of the user.

One or more of the fluid-permeable substrate and layer of fluid-impermeable dielectric material may be sufficiently resilient to enable the light emitter and photodetector to be positioned on opposite sides of the user's body part by mechanical deformation of the fluid-permeable substrate such that the photodetector can detect the transmitted light.

One or more of the fluid-permeable substrate and layer of fluid-impermeable dielectric material may be one or more of reversibly flexible, reversibly stretchable and reversibly compressible.

The light emitter and photodetector may be encapsulated within a fluid-impermeable material to inhibit their exposure to fluid in the surrounding environment.

The fluid may comprise one or more of a liquid and a gas.

The fluid may comprise one or more of water and oxygen.

The layer of fluid-impermeable dielectric material may comprise one or more of $SiO_x$, $SiN_x$, $AlO_x$, $Al_2O_3$, $AlN_x$ and $HfO_2$.

The one or more polymeric materials may comprise at least one of polyimide, polyethylene naphthalate and polyethylene terephthalate.

The light emitter may be one or more of a light-emitting diode, an organic light-emitting diode and an organic light-emitting transistor.

The light may comprise one or more of visible light, infrared light and ultraviolet light.

One or more components of the light emitter and photodetector may comprise graphene.

The layer of photosensitive material may comprise a quantum dot material.

The layer of fluid-impermeable dielectric material may be configured to prevent exposure of the light emitter to up to 50%, 60%, 70%, 80%, 90% or 100% of the fluid which has permeated through the fluid-permeable substrate.

The apparatus may be one or more of an electronic device, a portable electronic device, a portable telecommunications device, a mobile phone, a personal digital assistant, a tablet, a phablet, a desktop computer, a laptop computer, a server, a smartphone, a smartwatch, smart eyewear, a sensor, an $SpO_2$ sensor, a blood pressure sensor, a pulse sensor, and a module for one or more of the same.

According to a further aspect, there is provided a method of using an apparatus, the apparatus comprising a light emitter and a photodetector formed on a single fluid-permeable substrate such that the photodetector is able to detect light emitted by the light emitter after interaction of the light with a user of the apparatus, the photodetector comprising a channel member and respective source and drain electrodes configured to enable a flow of electrical current through the channel member between the source and drain electrodes, a layer of photosensitive material configured to vary the flow of electrical current through the channel member on exposure to light from the light emitter, and a gate electrode, wherein the apparatus comprises a layer of fluid-impermeable dielectric material configured to:

inhibit a flow of electrical current between the channel member and the gate electrode of the photodetector to enable the electrical conductance of the channel member to be controlled by a voltage applied to the gate electrode; and inhibit exposure of the light emitter to fluid which has permeated through the fluid-permeable substrate, the method comprising detecting, by the photodetector, light emitted by the light emitter after interaction of the light with a user of the apparatus.

According to a further aspect, there is provided a method of making an apparatus, the method comprising:

forming a light emitter and a photodetector on a single fluid-permeable substrate such that the photodetector is able to detect light emitted by the light emitter after interaction of the light with a user of the apparatus, the photodetector comprising a channel member and respective source and drain electrodes configured to enable a flow of electrical current through the channel member between the source and drain electrodes, a layer of photosensitive material configured to vary the flow of electrical current through the channel member on exposure to light from the light emitter, and a gate electrode; and forming a layer of fluid-impermeable dielectric material configured to:

inhibit a flow of electrical current between the channel member and the gate electrode of the photodetector to enable the electrical conductance of the channel member to be controlled by a voltage applied to the gate electrode; and inhibit exposure of the light emitter to fluid which has permeated through the fluid-permeable substrate.

Forming the light emitter and photodetector on a single fluid-permeable substrate may comprise depositing a layer of material which is common to both the light emitter and photodetector, and subsequently dividing the common layer of material into respective portions for the light emitter and photodetector after deposition.

The steps of any method disclosed herein do not have to be performed in the exact order disclosed, unless explicitly stated or understood by the skilled person.

Throughout the present specification, descriptors relating to relative orientation and position, such as "top", "bottom", "upper", "lower", "above" and "below", as well as any adjective and adverb derivatives thereof, are used in the sense of the orientation of the apparatus as presented in the drawings. However, such descriptors are not intended to be in any way limiting to an intended use of the described or claimed invention.

Corresponding computer programs for implementing one or more steps of the methods disclosed herein are also within the present disclosure and are encompassed by one or more of the described example embodiments.

One or more of the computer programs may, when run on a computer, cause the computer to configure any apparatus, including a circuit, controller, or device disclosed herein or perform any method disclosed herein. One or more of the computer programs may be software implementations, and the computer may be considered as any appropriate hardware, including a digital signal processor, a microcontroller, and an implementation in read only memory (ROM), erasable programmable read only memory (EPROM) or electronically erasable programmable read only memory (EEPROM), as non-limiting examples. The software may be an assembly program.

One or more of the computer programs may be provided on a computer readable medium, which may be a physical computer readable medium such as a disc or a memory device, or may be embodied as a transient signal. Such a transient signal may be a network download, including an internet download.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which.

DESCRIPTION OF SPECIFIC ASPECTS/EMBODIMENTS

There is a growing need for medical professionals to be able to monitor the health of their patients remotely. In order to enable remote monitoring, it is necessary to produce reliable sensor devices that are easy for the patients to use and which can be manufactured at a reasonable cost.

A number of medical devices are currently being developed which may be suitable for the remote monitoring of patients. These include light-based sensors which can be attached to part of the patient's body to provide information on his/her blood and cardiovascular system. For example, light-based sensors can provide information on oxygen content, blood pressure, pulse and heart rhythm. Of course, health sensors are also used by individuals without reference to remote monitoring by medical professionals, and by patients in the presence of medical professionals.

Figure 1A:
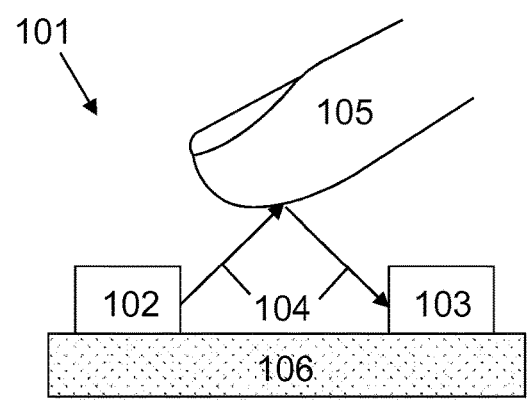
FIG. 1a shows a sensor comprising a photodetector configured to detect reflected light (cross-section)

FIG. 1a shows one example of a light-based sensor 101 which may be used for blood pressure, pulse or electrocardiography measurements. The apparatus 101 comprises a light emitter 102 and a photodetector 103 formed on a substrate 106 which are configured such that the photodetector 103 is able to detect light 104 emitted by the light emitter 102 after interaction of the light 104 with the patient. In this case, the sensor 101 is arranged such that the photodetector 103 is able to detect light 104 which has been reflected from a body part 105 of the user, such as a finger, toe or ear lobe. Infrared light 104 (e.g. from an infrared diode 102) is directed into the patient's tissue 105 and is reflected back onto the photodetector 103 (e.g. a phototransistor) in quantities related to the amount of blood currently in the artery. When the heart pumps, the user's blood pressure rises sharply, and so does the amount of infrared light 104 received by the photodetector 103. The patient's pulse and heart rhythm can therefore be determined from the pattern of peaks in the detected signal. In addition, the blood pressure can be derived from the time it takes for a pulse to travel down the artery (i.e. the Pulse Wave Transit Time, PWTT) using the waveform of blood pressure pulses.

Figure 1B:
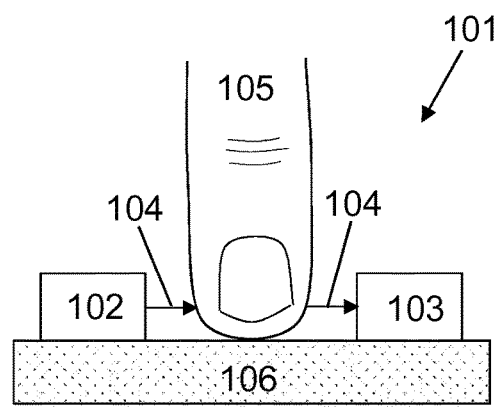
FIG. 1b shows a sensor comprising a photodetector configured to detect transmitted light (cross-section)

FIG. 1b shows an example of a light-based sensor 101 which may be used for $SpO_2$ measurements. The term $SpO_2$ refers to the percentage of haemoglobin molecules in the arterial blood which are saturated with oxygen, as determined by pulse oximetry. As per the example shown in FIG. 1a, the apparatus 101 comprises a light emitter 102 and photodetector 103 formed on a substrate 106 which are configured such that the photodetector 103 is able to detect light 104 emitted by the light emitter 102 after interaction of the light 104 with the patient. In this example, however, the sensor 101 is arranged such that the photodetector 103 is able to detect light 104 which has been transmitted through a body part 105 of the user. Most $SpO_2$ sensors work on extremities such as a finger, toe or ear lobe. Red and infrared light 104 (e.g. from respective light emitting diodes 102) is passed through the patient's tissue 105 onto the photodetector 103. Much of the light 104 is absorbed by tissue, bone and venous blood, but these amounts do not change dramatically over short periods of time. However, since the amount of arterial blood varies with pulsation, the amount of light 104 absorbed by this blood does vary over short periods of time and can be isolated from the other components. The photodetector 103 measures the amount of red and infrared light 104 received, which provides an indication of the amount of oxygen bound to the haemoglobin in the arterial blood. Oxygenated haemoglobin absorbs more infrared light than red light, whilst deoxygenated haemoglobin absorbs more red light than infrared light. Therefore, by comparing the amounts of red and infrared light 104 received, the sensor 101 is able to calculate the percentage of haemoglobin molecules in the arterial blood which are saturated with oxygen.

In some cases it may be desirable to monitor a patient's health continuously over long periods of time. To help ensure that the measurements are consistent and reliable during this time, and without interfering too much with the patient's day-to-day life, the sensor apparatus 101 may be attached to the patient. In this scenario, the apparatus 101 should ideally be formed from resilient materials to allow it to conform to the patient's body 105. This improves the comfort of the wearable device 101 and helps to prevent damage caused by mechanical deformation during movement of the patient.

Figure 2:
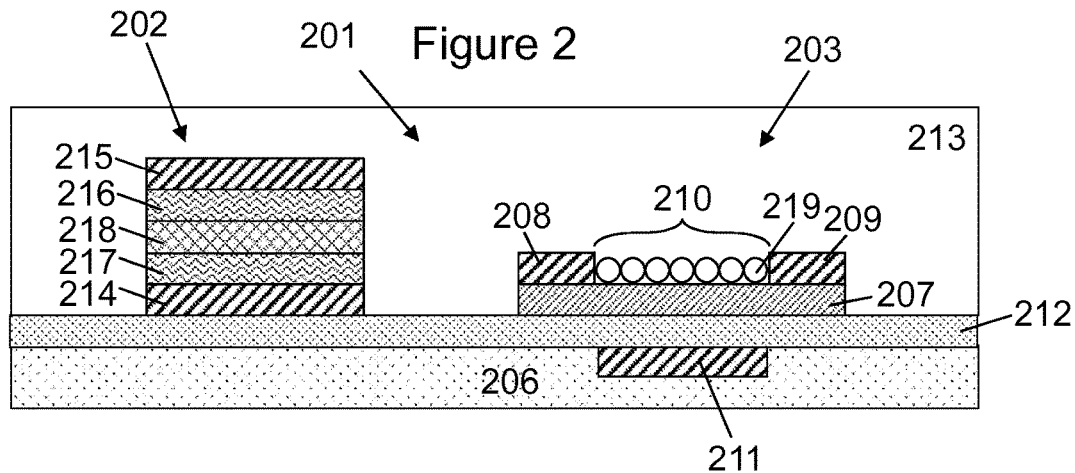
FIG. 2 shows one example of the present apparatus (cross-section)

FIG. 2 shows one example of the present apparatus 201. The apparatus 201 comprises a light emitter 202 and a photodetector 203 formed on a single fluid-permeable substrate 206 such that the photodetector 203 is able to detect light emitted by the light emitter 202 after interaction of the light with a user of the apparatus. The photodetector 203 comprises a channel member 207 and respective source 208 and drain 209 electrodes configured to enable a flow of electrical current through the channel member 207 between the source 208 and drain 209 electrodes, a layer of photosensitive material 210 configured to vary the flow of electrical current through the channel member 207 on exposure to light from the light emitter 202, and a gate electrode 211. The apparatus 201 also comprises a layer of fluid-impermeable dielectric material 212 configured to inhibit a flow of electrical current between the channel member 207 and gate electrode 211 of the photodetector 203 to enable the electrical conductance of the channel member 207 to be controlled by a voltage applied to the gate electrode 211. Furthermore, the layer of fluid-impermeable dielectric material 212 is also configured to inhibit exposure of the light emitter 202 (and overlying components of the photodetector 203) to fluid which has permeated through the fluid-permeable substrate 206.

The layer of fluid-impermeable dielectric material 212 therefore serves as both a gate insulator for the photodetector 203, and as a fluid barrier for the light emitter 202/photodetector 203. The presence of the fluid-impermeable dielectric layer 212 allows plastic substrates 206 to be used without the risk of damage to the overlying components 202, 203 caused by water, oxygen or other fluids which have permeated through the plastic substrate 206. Plastic substrates, which are typically fluid permeable due to their lack of ordering, can be used instead of conventional silicon wafer substrates to take advantage of the flexible/stretchable nature of the plastic. Furthermore, in some cases, the presence of the fluid-impermeable dielectric layer 212 can also create a smoother surface for the overlying components 202, 203 (which advantageously reduces electrostatic interactions caused by the irregular surfaces of plastic substrates) and help to dissipate heat produced by these components (which could otherwise damage plastic substrates due to their relatively low melting points).

In practice, the fluid-impermeable dielectric material 212 may be configured to prevent exposure of the light emitter 202 and photodetector 203 to up to 50%, 60%, 70%, 80%, 90% or 100% of the fluid which has permeated through the fluid-permeable substrate 206. The apparatus of FIG. 2 also comprises a layer of fluid-impermeable material 213 configured to encapsulate the light emitter 202 and photodetector 203 to inhibit their exposure to fluid in the surrounding environment (e.g. water droplets in the air).

The dual functionality of the fluid-impermeable dielectric material 212 reduces the number of fabrication steps used to form the apparatus 201 and results in a thinner, more compact device 201. In some cases, the layer of fluid-impermeable dielectric material 212 may also be configured to facilitate the dissipation of heat produced by one or more of the light emitter 202 and photodetector 203, thus preventing the underlying substrate 206 from melting.

The light emitter 202 may be one or more of a light-emitting diode, an organic light-emitting diode and an organic light-emitting transistor. In the example shown in FIG. 2, the light emitter 202 is an organic light-emitting diode comprising an anode 214 and cathode 215 separated from one another by an electron transporting layer 216, a hole transporting layer 217 and an emitting layer 218. When a voltage is applied between the anode 214 and cathode 215, electrons flow from the cathode 215 through the electron transporting layer 216 towards the anode 214. Simultaneously, electron-holes flow from the anode 214 through the hole transporting layer 217 towards the cathode 215. Since the electron transporting layer 216 blocks the flow of holes and the hole transporting layer 217 blocks the flow of electrons, the electrons and holes recombine at the emitting layer 218 positioned therebetween. Recombination of the electrons and holes results in the emission of a light photon from the emitting layer 218 having a frequency which is given by the difference in energy between the highest occupied and lowest unoccupied molecular orbitals of the electron 216 and hole 217 transporting layers. For example, the band gap may be such that the emitted light comprises one or more of visible, infrared and ultraviolet light.

Typically, the upper electrode 215 (in this case, the cathode) would be substantially optically transparent to allow the generated light photons to exit the top surface of the light emitter 202. To increase the efficiency of the light emitter 202, the lower electrode 214 (in this case, the anode) may be formed from a reflective material configured to redirect stray light photons towards the top surface of the light emitter 202. Additionally or alternatively, the light emitter 202 may comprise a separate layer of reflective material positioned beneath the lower electrode 214. In view of the above, the upper electrode 215 may comprise graphene or indium-tin-oxide, and the lower electrode 214 may comprise silver or aluminium.

Regarding the photodetector 203, the photosensitive material 210 shown in the example of FIG. 2 is a quantum dot material comprising a plurality of quantum dots 219 coated with surface ligands, and the channel member 207 comprises a two-dimensional material. The quantum dots 219 may comprise one or more of CdSe, CdS, PbSe, PbS, ZnO, ZnS, CZTS, $Cu_2S$, $Bi_2S_3$, $Ag_2S$, HgTe, CdSe, CdHgTe, InAs, InSb, Ge and CIS; the surface ligands may comprise one or more of 1,2-ethanedithiol, pyridine, butylamine and 1,3-benzenedithiol; and the two-dimensional material may comprise one or more of graphene, $MoS_2$, $WS_2$, $MoSe_2$, $WSe_2$ and $WTe_2$. When light from the light emitter 202 is incident on the quantum dot material 210, electron-hole pairs are generated within the quantum dots 219. After generation of these electron-hole pairs, either the electrons or the holes are transferred to the channel member 207 (depending on the particular surface ligands) leaving the remaining charge carriers localised on the quantum dots 219. The remaining charge carriers then gate the channel member 207 causing a change in the current flowing therethrough. In this way, the change in electrical current is indicative of the amount of light incident on the photodetector 203. The photosensitive material 210 of the present apparatus 201 is not limited to quantum dot materials, however. For example, the photosensitive material 210 may be a photodiode comprising a p-n or PIN junction.

The gate electrode 211 of the photodetector 203 in FIG. 2 is embedded within the fluid-permeable substrate 206 such that the layer of fluid-impermeable dielectric material 212 is positioned between the embedded gate electrode 211 and the channel member 207. This "back-gate" configuration allows the gate electrode 211 to tune the conductance of the channel member 207 by increasing or decreasing the number of charge carriers to increase the sensitivity of the photodetector 203. When the channel member 207 comprises graphene, the gate electrode 211 can also be used to switch between p-type conductance and n-type conductance by changing the Dirac point location.

Furthermore, by embedding the gate electrode 211 within the fluid-permeable substrate 206, the fluid-impermeable dielectric material 212 can be deposited onto the fluid-permeable substrate 206 as a continuous layer thus providing a planar surface on which to form the light emitter 202 and photodetector 203. In some cases, the thickness of dielectric material 212 required to inhibit exposure of the light emitter 202 to fluid which has permeated through the fluid-permeable substrate 206 may be different than the thickness of dielectric material 212 required to inhibit a flow of electrical current between the gate electrode 211 and channel member 207 of the photodetector 203. In this scenario, the fluid-impermeable dielectric material 212 on which the light emitter 202 is formed may have a different thickness than the fluid-impermeable dielectric material 212 on which the photodetector 203 is formed (e.g. by depositing a non-uniform layer of dielectric material 212 on top of the fluid-permeable substrate 206).

Non-embedded embodiments are also possible. For example, the gate electrode 211 may be formed on the upper surface of the fluid-permeable substrate 206 with the layer of fluid-impermeable dielectric material 212 deposited thereon. This would, however, result in a non-planar (but not necessarily discontinuous) layer of fluid-impermeable dielectric material 212.

The fluid-permeable substrate 206 may comprise one or more polymeric materials configured to provide the required resilience (e.g. reversibly flexible, stretchable and/or compressible). These polymeric materials may comprise at least one of HD Microsystems™ PI-2545, PI-2610 or PI-2525, polyimide, polyethylene naphthalate and polyethylene terephthalate. Substrates formed from polymeric materials often have irregular surfaces which create a poor interface with the overlying layers of material. It has been found, however, that the presence of the fluid-impermeable dielectric material 212 on top of the fluid-permeable substrate 206 can advantageously reduce the surface roughness. For example, a 25 nm layer of $Al_2O_3$ on top of a polyethylene naphthalate substrate exhibits a surface roughness of around 1 nm. In general, the layer of fluid-impermeable dielectric material 212 may have a thickness of between 10 and 200 nm, and a surface roughness of less than 1 nm, 5 nm, 10 nm or 25 nm. Suitable dielectric materials include $SiO_x$, $SiN_x$, $AlO_x$, $Al_2O_3$, $AlN_x$ and $HfO_2$.

Figure 3A:
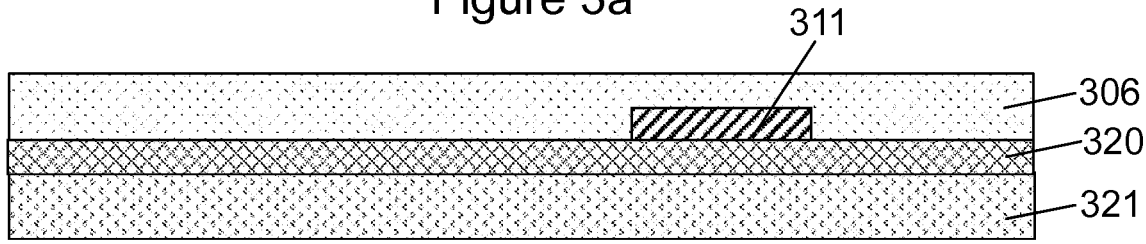
FIGS. 3a-3d show one method of making the apparatus of FIG. 2 (cross-section)

FIGS. 3a-3d illustrate one method of forming the present apparatus. First, a layer of release material 320 is deposited on a carrier wafer 321 (e.g. via chemical vapour deposition) followed by the deposition of a gate electrode 311 (e.g. via evaporation or sputtering through a photoresist mask). The release material 320 may comprise one or more of a refractory metal, a ceramic, SiO, $SiO_2$, Mo, W, $Al_2O_3$ and $Si_3N_4$; the carrier wafer 321 may comprise one or more of silicon, quartz and sapphire; and the gate electrode 311 may comprise one or more of a metal, alloy, gold, silver, copper, aluminium, indium-tin-oxide and graphene. A layer of polymeric material 306 is then deposited on top of the layer of release material 320 such that it encapsulates the gate electrode 311 (FIG. 3a). Deposition of the polymeric material may be performed via spin coating, bar coating or spray coating a liquid polymer and curing to cross-link, or by hot embossing a polymer foil (i.e. heating above the glass transition temperature and imprinting).

Figure 3B:
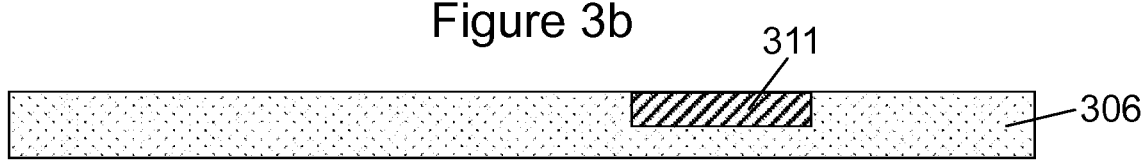
Figure 3C:
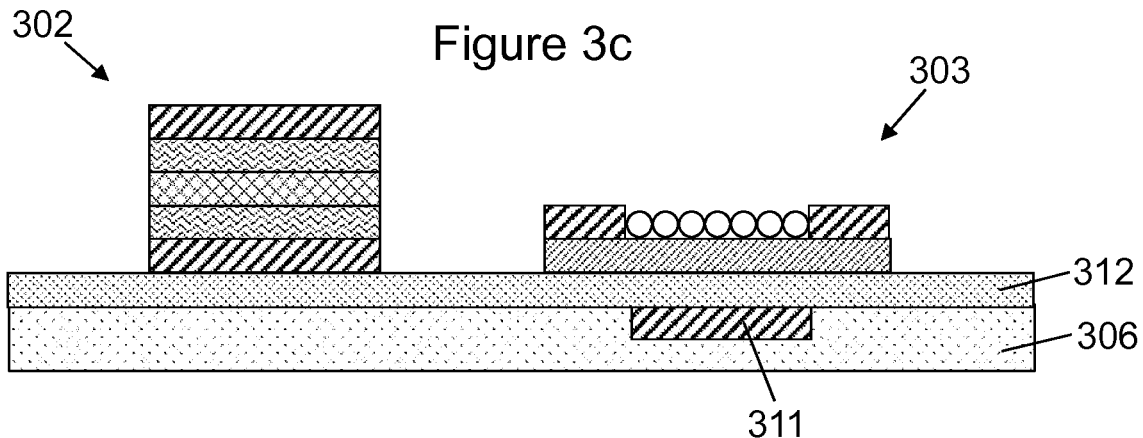
Figure 3D:
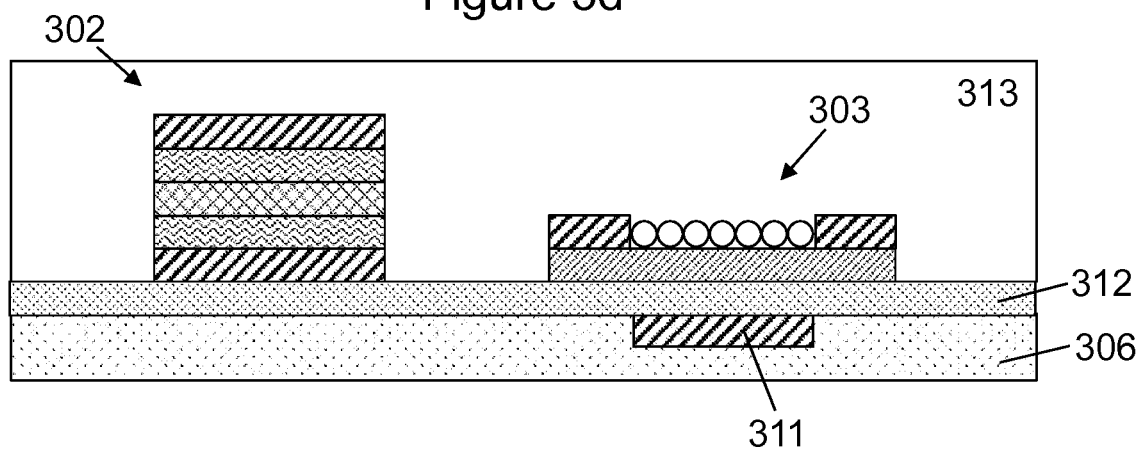

The layer of release material 320 is then etched (e.g. via wet chemical etching using hydrofluoric acid if etching silicon oxide) to remove the release material 320 and carrier wafer 321, and the stack is turned upside down (e.g. using the polymeric supporting substrate 306 for handling) so that the layer of polymeric material 306 is at the bottom of the stack (FIG. 3b). A layer of fluid-impermeable dielectric material 312 is then formed on the polymeric substrate 306 (e.g. via atomic layer deposition or chemical vapour deposition), and the constituent layers of the light emitter 302 and photodetector 303 are built-up on top of the fluid-impermeable dielectric material 312 using techniques known in the art (FIG. 3c). Finally, a further fluid-impermeable material 313 (typically an electrically insulating material such as a polymer or oxide) is then deposited over the layer of fluid-impermeable dielectric material 312 such that it encapsulates the light emitter 302 and photodetector 303 (FIG. 3d).

The present apparatus may be used in the reflective or transmissive modes illustrated in FIGS. 1a and 1b, respectively. In the reflective mode, the light emitter 302 and photodetector 303 are formed on the fluid-permeable substrate 306 such that the photodetector 303 is able to detect light emitted by the light emitter 302 after reflection of the light from a body part of the user. In the transmissive mode, on the other hand, the light emitter 302 and photodetector 303 are formed on the fluid-permeable substrate 306 such that the photodetector 303 is able to detect light emitted by the light emitter 302 after transmission of the light through a body part of the user.

Figure 4:
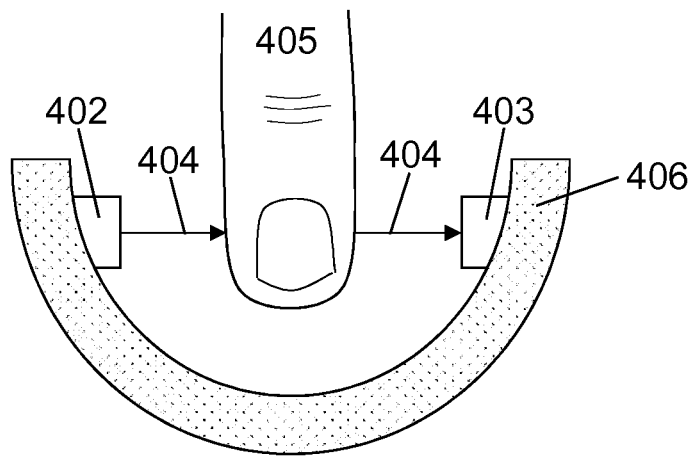
FIG. 4 shows another example of the present apparatus comprising a photodetector configured to detect transmitted light (cross-section)

FIG. 4 shows another example of the present apparatus 401 configured for use in the transmissive mode. One reason for using a polymeric substrate is to make the apparatus 401 sufficiently resilient that it is able to conform to the user's body 405. In some cases, therefore, the fluid-permeable substrate 406 may be sufficiently resilient to enable the light emitter 402 and photodetector 403 to be positioned on opposite sides of the user's body part 405 by mechanical deformation of the fluid-permeable substrate 406 such that the photodetector 403 can detect the transmitted light 404. In this example, the light emitter 402 and photodetector 403 are positioned on opposite sides of the user's finger 405, but they could be attached to the user's toe or ear lobe instead.

It is important that, in the deformed state, the layer of fluid-impermeable dielectric material is still able to inhibit a flow of electrical current between the channel member and gate electrode of the photodetector 403, and inhibit exposure of the light emitter 402/photodetector 403 to fluid which has permeated through the fluid-permeable substrate 406. In some cases, the layer of fluid-impermeable dielectric material may provide this functionality in both the deformed and relaxed states, whilst in other cases, the layer of fluid-impermeable dielectric material may only provide this functionality in the mechanical state in which it is intended to be used (i.e. the deformed state in FIG. 4).

Although the above examples utilise resilient polymeric substrates, the fluid-permeable substrate is not limited to such materials. For example, the fluid-permeable substrate could comprise other resilient materials which are inherently fluid-permeable, such as natural or synthetic sponge or a textile.

Figure 5:
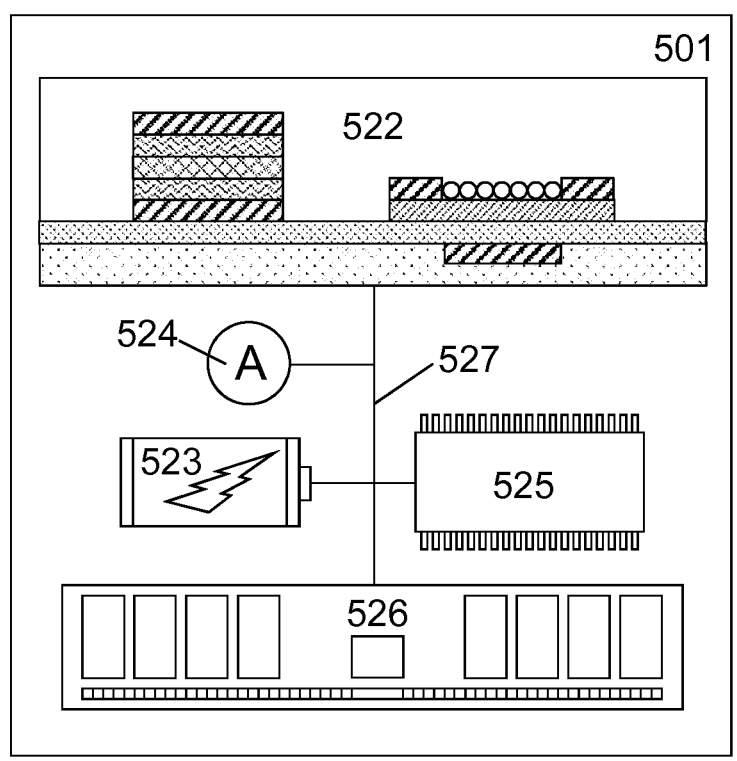
FIG. 5 shows another example of the present apparatus (schematic)

FIG. 5 shows another example of the present apparatus 501. The apparatus 501 may be one or more of an electronic device, a portable electronic device, a portable telecommunications device, a mobile phone, a personal digital assistant, a tablet, a phablet, a desktop computer, a laptop computer, a server, a smartphone, a smartwatch, smart eyewear, a sensor, an $SpO_2$ sensor, a blood pressure sensor, a pulse sensor, and a module for one or more of the same. In the example shown, the apparatus 501 comprises the various components described previously (denoted collectively by reference numeral 522), a power source 523, an ammeter 524, a processor 525 and a storage medium 526, which are electrically connected to one another by a data bus 527.

The processor 525 is configured for general operation of the apparatus 501 by providing signalling to, and receiving signalling from, the other components to manage their operation. The storage medium 526 is configured to store computer code configured to perform, control or enable operation of the apparatus 501. The storage medium 526 may also be configured to store settings for the other components. The processor 525 may access the storage medium 526 to retrieve the component settings in order to manage the operation of the other components.

Under the control of the processor 525, the power source 523 is configured to apply a voltage between the cathode and anode of the light emitter to generate light photons for interaction with the user. In addition, the power source 523 is configured to apply a voltage between the source and drain electrodes of the photodetector to enable a flow of electrical current through the channel member, and a further voltage to the gate electrode to control the electrical conductance of the channel member.

The ammeter 524 is configured to measure the current through the channel member of the photodetector so that any changes in current caused by light from the light emitter can be determined. Based on these changes in current, one or more parameters relating to the user's health can be calculated (e.g. blood pressure, oxygen content, pulse and heart rhythm). The user's health parameters may be calculated automatically by the processor 525 or manually by the user or a health professional.

The processor 525 may be a microprocessor, including an Application Specific Integrated Circuit (ASIC). The storage medium 526 may be a temporary storage medium such as a volatile random access memory. On the other hand, the storage medium 526 may be a permanent storage medium 526 such as a hard disk drive, a flash memory, or a non-volatile random access memory. The power source 523 may comprise one or more of a primary battery, a secondary battery, a capacitor, a supercapacitor and a battery-capacitor hybrid.

Figure 6A:
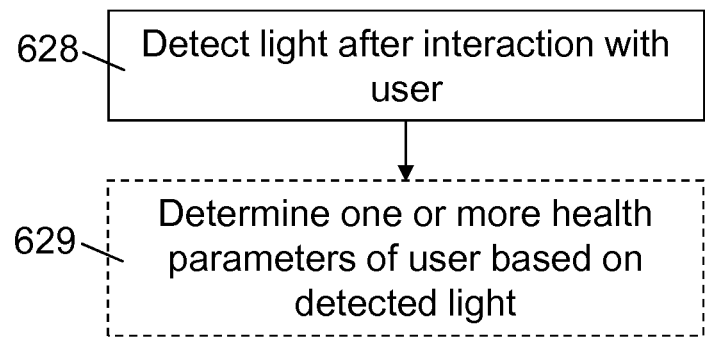
FIG. 6a shows a method of using the present apparatus (flow chart)

FIG. 6a shows schematically the main steps 628-629 of a method of using the present apparatus. The method generally comprises: detecting, by a photodetector, light emitted by a light emitter after interaction of the light with a user of the apparatus 628; and determining one or more health parameters of the user based on the detected light 629.

Figure 6B:
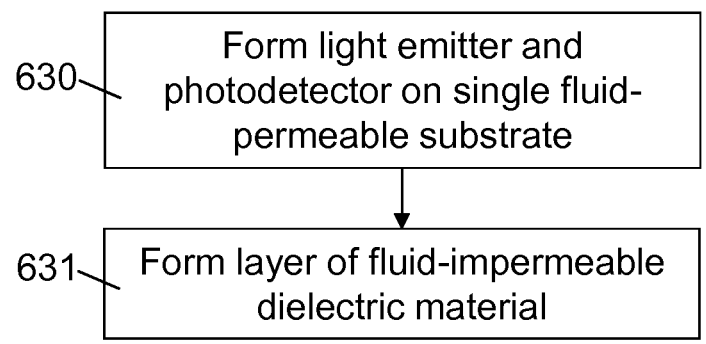
FIG. 6b shows a method of making the present apparatus (flow chart)

FIG. 6b shows schematically the main steps 630-631 of a method of making the present apparatus. The method generally comprises: forming a light emitter and a photodetector on a single fluid-permeable substrate such that the photodetector is able to detect light emitted by the light emitter after interaction of the light with a user of the apparatus 630;

and forming a layer of fluid-impermeable dielectric material configured to inhibit a flow of electrical current between a channel member and the gate electrode of the photodetector to enable the electrical conductance of the channel member to be controlled by a voltage applied to the gate electrode, and inhibit exposure of the light emitter to fluid which has permeated through the fluid-permeable substrate 631.

Figure 7:
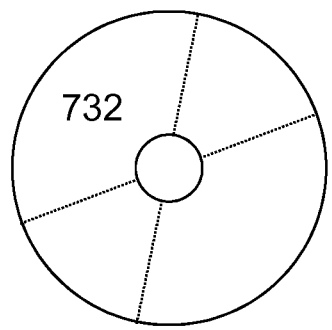
FIG. 7 shows a computer-readable medium comprising a computer program configured to perform, control or enable a method described herein (schematic).

FIG. 7 illustrates schematically a computer/processor readable medium 732 providing a computer program according to one embodiment. The computer program may comprise computer code configured to perform, control or enable one or more of the method steps 628-631 of FIG. 6a or 6b. In this example, the computer/processor readable medium 732 is a disc such as a digital versatile disc (DVD) or a compact disc (CD). In other embodiments, the computer/processor readable medium 732 may be any medium that has been programmed in such a way as to carry out an inventive function. The computer/processor readable medium 732 may be a removable memory device such as a memory stick or memory card (SD, mini SD, micro SD or nano SD).

Other embodiments depicted in the figures have been provided with reference numerals that correspond to similar features of earlier described embodiments. For example, feature number 1 can also correspond to numbers 101, 201, 301 etc. These numbered features may appear in the figures but may not have been directly referred to within the description of these particular embodiments. These have still been provided in the figures to aid understanding of the further embodiments, particularly in relation to the features of similar earlier described embodiments.

It will be appreciated to the skilled reader that any mentioned apparatus/device and/or other features of particular mentioned apparatus/device may be provided by apparatus arranged such that they become configured to carry out the desired operations only when enabled, e.g. switched on, or the like. In such cases, they may not necessarily have the appropriate software loaded into the active memory in the non-enabled (e.g. switched off state) and only load the appropriate software in the enabled (e.g. on state). The apparatus may comprise hardware circuitry and/or firmware. The apparatus may comprise software loaded onto memory. Such software/computer programs may be recorded on the same memory/processor/functional units and/or on one or more memories/processors/functional units.

In some embodiments, a particular mentioned apparatus/device may be pre-programmed with the appropriate software to carry out desired operations, and wherein the appropriate software can be enabled for use by a user downloading a "key", for example, to unlock/enable the software and its associated functionality. Advantages associated with such embodiments can include a reduced requirement to download data when further functionality is required for a device, and this can be useful in examples where a device is perceived to have sufficient capacity to store such pre-programmed software for functionality that may not be enabled by a user.

It will be appreciated that any mentioned apparatus/circuitry/elements/processor may have other functions in addition to the mentioned functions, and that these functions may be performed by the same apparatus/circuitry/elements/processor. One or more disclosed aspects may encompass the electronic distribution of associated computer programs and computer programs (which may be source/transport encoded) recorded on an appropriate carrier (e.g. memory, signal).

It will be appreciated that any "computer" described herein can comprise a collection of one or more individual processors/processing elements that may or may not be located on the same circuit board, or the same region/position of a circuit board or even the same device. In some embodiments one or more of any mentioned processors may be distributed over a plurality of devices. The same or different processor/processing elements may perform one or more functions described herein.

It will be appreciated that the term "signalling" may refer to one or more signals transmitted as a series of transmitted and/or received signals. The series of signals may comprise one, two, three, four or even more individual signal components or distinct signals to make up said signalling. Some or all of these individual signals may be transmitted/received simultaneously, in sequence, and/or such that they temporally overlap one another.

With reference to any discussion of any mentioned computer and/or processor and memory (e.g. including ROM, CD-ROM etc), these may comprise a computer processor, Application Specific Integrated Circuit (ASIC), field-programmable gate array (FPGA), and/or other hardware components that have been programmed in such a way to carry out the inventive function.

The applicant hereby discloses in isolation each individual feature described herein and any combination of two or more such features, to the extent that such features or combinations are capable of being carried out based on the present specification as a whole, in the light of the common general knowledge of a person skilled in the art, irrespective of whether such features or combinations of features solve any problems disclosed herein, and without limitation to the scope of the claims. The applicant indicates that the disclosed aspects/embodiments may consist of any such individual feature or combination of features. In view of the foregoing description it will be evident to a person skilled in the art that various modifications may be made within the scope of the disclosure.

While there have been shown and described and pointed out fundamental novel features as applied to different embodiments thereof, it will be understood that various omissions and substitutions and changes in the form and details of the devices and methods described may be made by those skilled in the art without departing from the spirit of the invention. For example, it is expressly intended that all combinations of those elements and/or method steps which perform substantially the same function in substantially the same way to achieve the same results are within the scope of the invention. Moreover, it should be recognized that structures and/or elements and/or method steps shown and/or described in connection with any disclosed form or embodiment may be incorporated in any other disclosed or described or suggested form or embodiment as a general matter of design choice. Furthermore, in the claims means-plus-function clauses are intended to cover the structures described herein as performing the recited function and not only structural equivalents, but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

The invention claimed is:

1. An apparatus comprising:
   a fluid-permeable substrate;
   a gate electrode of a photodetector embedded within the fluid-permeable substrate;

a layer of fluid-impermeable dielectric material covering the fluid-permeable substrate and the gate electrode;
a light emitter on the layer of fluid-impermeable dielectric material;
a channel member, a source electrode, and a drain electrode of the photodetector on the layer of fluid-impermeable dielectric material, the source electrode and the drain electrode being separated from one another on the channel member, the source electrode and the drain electrode enabling a flow of electrical current through the channel member between the source electrode and the drain electrode, a layer of photosensitive material being included between the source electrode and the drain electrode on the channel member, the layer of photosensitive material being configured to vary the flow of electrical current through the channel member on exposure to light from the light emitter, the channel member being separated from the gate electrode by the layer of fluid-impermeable dielectric material,
wherein the layer of fluid-impermeable dielectric material inhibits the flow of electrical current between the channel member and the gate electrode to enable the electrical conductance of the channel member to be controlled by a voltage applied to the gate electrode, and inhibits exposure of the light emitter to fluid permeating through the fluid-permeable substrate.

2. The apparatus of claim 1, wherein the fluid-permeable substrate comprises one or more resilient polymeric materials.

3. The apparatus of claim 1, wherein the layer of fluid-impermeable dielectric material is configured to facilitate the dissipation of heat produced by the light emitter.

4. The apparatus of claim 1, wherein the fluid-impermeable dielectric material under the light emitter has a different thickness than the fluid-impermeable dielectric material under the channel member.

5. The apparatus of claim 1, wherein the layer of fluid-impermeable dielectric material has a thickness between 10 nm and 200 nm, and a surface roughness of less than 25 nm.

6. The apparatus of claim 1, wherein the light emitter and the channel member, the source electrode, and the drain electrode of the photodetector are formed on the layer of fluid-impermeable dielectric material to enable the photodetector to detect light emitted by the light emitter after reflection of the light from a body part of a user or transmission of the light through the body part of the user.

7. The apparatus of claim 6, wherein the fluid-permeable substrate and the layer of fluid-impermeable dielectric material are resilient to enable the light emitter and photodetector to be positioned on opposite sides of the body part of the user by mechanical deformation of the fluid-permeable substrate and the layer of fluid-impermeable dielectric material such that the photodetector detects light transmitted through the body part of the user.

8. The apparatus of claim 1, wherein the light emitter and photodetector are encapsulated within a fluid-impermeable material to inhibit their exposure to fluid in the surrounding environment.

9. The apparatus of claim 1, wherein the fluid comprises water, or oxygen, or both water and oxygen.

10. The apparatus of claim 1, wherein the layer of fluid-impermeable dielectric material prevents exposure of the light emitter to 50% or more of the fluid permeating through the fluid-permeable substrate.

11. The apparatus of claim 1, wherein the apparatus is one or more of an electronic device, a portable electronic device, a portable telecommunications device, a mobile phone, a personal digital assistant, a tablet, a phablet, a desktop computer, a laptop computer, a server, a smartphone, a smartwatch, smart eyewear, a sensor, an SpO2 sensor, a blood pressure sensor, a pulse sensor, and a module for one or more of the same.

12. A method of making an apparatus, the method comprising:
providing a fluid-permeable substrate;
forming a gate electrode of a photodetector embedded within the fluid-permeable substrate;
covering the fluid-permeable substrate and the gate electrode with a layer of fluid-impermeable dielectric material;
forming a light emitter on the layer of fluid-impermeable dielectric material;
forming a channel member, a source electrode, and a drain electrode of the photodetector on the layer of fluid-impermeable dielectric material, the source electrode and the drain electrode being separated from one another on the channel member, the source electrode and the drain electrode enabling a flow of electrical current through the channel member between the source electrode and the drain electrode,
forming a layer of photosensitive material between the source electrode and the drain electrode on the channel member, the layer of photosensitive material being configured to vary the flow of electrical current through the channel member on exposure to light from the light emitter, the channel member being separated from the gate electrode by the layer of fluid-impermeable dielectric material,
wherein the layer of fluid-impermeable dielectric material inhibits the flow of electrical current between the channel member and the gate electrode to enable the electrical conductance of the channel member to be controlled by a voltage applied to the gate electrode, and inhibits exposure of the light emitter to fluid permeating through the fluid-permeable substrate.

13. The method of claim 12, wherein the fluid-permeable substrate is provided comprising one or more resilient polymeric materials.

14. The method of claim 12, wherein the layer of fluid-impermeable dielectric material is configured via at least the covering to facilitate dissipation of heat produced by the light emitter.

15. The method of claim 12, wherein the fluid-impermeable dielectric material under the light emitter is formed to have a different thickness than a thickness of the fluid-impermeable dielectric material under the channel member.

16. The method of claim 12, wherein the layer of fluid-impermeable dielectric material is formed to have a thickness between 10 nm and 200 nm, and a surface roughness of less than 25 nm.

17. The method of claim 12, wherein the light emitter and the channel member, the source electrode, and the drain electrode of the photodetector are formed on the layer of fluid-impermeable dielectric material to enable the photodetector to detect light emitted by the light emitter after reflection of the light from a body part of a user or transmission of the light through the body part of the user.

18. The method of claim 17, wherein the fluid-permeable substrate and the layer of fluid-impermeable dielectric material are formed to be resilient to enable the light emitter and photodetector to be positioned on opposite sides of the body part of the user by mechanical deformation of the fluid-permeable substrate and the layer of fluid-impermeable dielectric material such that the photodetector detects light transmitted through the body part of the user.

19. The method of claim 12, wherein the light emitter and photodetector are formed to be encapsulated within a fluid-impermeable material to inhibit their exposure to fluid in the surrounding environment.

20. The method of claim 12, wherein the fluid comprises water, or oxygen, or both water and oxygen.

* * * * *